(12) United States Patent
Nguyen et al.

(10) Patent No.: US 12,036,416 B2
(45) Date of Patent: Jul. 16, 2024

(54) WEARABLE CARDIOVERTER DEFIBRILLATOR (WCD) SYSTEM WITH WIRELESS BATTERY CHARGING

(71) Applicant: West Affum Holdings Corp., Grand Cayman (KY)

(72) Inventors: Quan H. Nguyen, Renton, WA (US); Robert R. Buchanan, Bothell, WA (US); Dallas E. Meeker, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

(21) Appl. No.: 17/246,371

(22) Filed: Apr. 30, 2021

(65) Prior Publication Data
US 2022/0143416 A1 May 12, 2022

Related U.S. Application Data (60) Provisional application No. 63/111,338, filed on Nov. 9, 2020.

(51) Int. Cl.
*A61N 1/39* (2006.01)
*A61N 1/04* (2006.01)

(52) U.S. Cl.
CPC ........... *A61N 1/3904* (2017.08); *A61N 1/046* (2013.01); *A61N 1/3925* (2013.01); *A61N 1/3968* (2013.01); *A61N 1/3975* (2013.01); *A61N 1/3993* (2013.01)

(58) Field of Classification Search
CPC .. A61N 1/0484; A61N 1/3904; A61N 1/3625; A61N 1/3787
See application file for complete search history.

(56) References Cited

U.S. PATENT DOCUMENTS

| | | | |
|---|---|---|---|
| 3,724,455 A | 4/1973 | Unger | |
| 4,583,524 A | 4/1986 | Hutchins | |
| 4,619,265 A | 10/1986 | Morgan et al. | |
| 4,928,690 A | 5/1990 | Heilman et al. | |
| 4,955,381 A | 9/1990 | Way et al. | |
| 5,078,134 A * | 1/1992 | Heilman ................ | A61N 1/046 607/142 |
| 5,228,449 A | 7/1993 | Christ et al. | |
| 5,348,008 A | 9/1994 | Born et al. | |
| 5,353,793 A | 10/1994 | Born | |

(Continued)

FOREIGN PATENT DOCUMENTS

| | | |
|---|---|---|
| EP | 3380189 B1 | 10/2018 |
| WO | 1998039061 A2 | 9/1998 |
| WO | 2012064604 A1 | 5/2012 |

OTHER PUBLICATIONS

Waters, Benjamin H et al., "Electrical power to run ventricular assist devices using the Free-range Resonant Electrical Energy Delivery system", The Journal of Heart and Lung Transplantation, vol. 37, No. 12, Dec. 2018, p. 1467-1475.

(Continued)

*Primary Examiner* — George R Evanisko
(74) *Attorney, Agent, or Firm* — Polsinelli PC (57) ABSTRACT

Technologies and implementations for a wearable healthcare system having an irremovable wirelessly chargeable energy storage device. The technologies and implementations facilitate at least continual monitoring.

16 Claims, 4 Drawing Sheets

(56) References Cited

U.S. PATENT DOCUMENTS

| | | | |
|---|---|---|---|
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,618,208 A | 4/1997 | Crouse et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,212,430 B1* | 4/2001 | Kung | A61M 60/178 607/61 |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Inder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,827,889 B2 | 9/2014 | Smith et al. | |
| 8,897,860 B2 | 11/2014 | Volpe et al. | |
| 8,901,779 B2 | 12/2014 | Kesler et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,415,149 B2 | 8/2016 | Smith et al. | |
| 9,454,219 B2 | 9/2016 | Volpe et al. | |
| 9,592,403 B2 | 3/2017 | Sullivan | |
| 9,878,171 B2 | 1/2018 | Kaib | |
| 10,561,881 B2* | 2/2020 | Matsuura | A61N 1/0452 |
| 10,719,134 B2* | 7/2020 | Aman | G06F 3/0346 |
| 10,886,761 B1* | 1/2021 | Schobben | A61N 1/3787 |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1* | 1/2009 | Weintraub | A61N 1/3904 601/84 |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0350635 A1* | 11/2014 | Strother | A61N 1/36082 607/45 |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2017/0181703 A1* | 6/2017 | Kaib | A61B 5/25 |
| 2017/0319082 A1 | 11/2017 | Sayme | |
| 2021/0322764 A1* | 10/2021 | Mauger | H04R 25/554 |
| 2022/0104996 A1* | 4/2022 | Bennett | A61H 19/30 |

OTHER PUBLICATIONS

"Cota: Real Wireless Power", Ossia, Nov. 9, 2020.

Smith, Joshua R., "Freed (Free-range Resonant Electrical Energy Delivery): A tether-free Left Ventricular Assist Device (LVAD)", Sensor Systems Laboratory, Nov. 9, 2020.

Schlosser, Kurt, "Seattle startup WiBotic secures FCC approval for wireless system to charge robots, drones and more", https://www.geekwire.com/author/kurt/), Aug. 6, 2020 at 11:38 am.

Boyle, Alan, "Wibotic raises $5.7M to boost wireless systems for charging up robots and drones", https://www.geekwire.com/author/alanboyle/), Jun. 11, 2020 at 9:01 am.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

WEARABLE CARDIOVERTER DEFIBRILLATOR (WCD) SYSTEM WITH WIRELESS BATTERY CHARGING

RELATED APPLICATION

This application claims benefit of priority to U.S. Provisional Patent Application Ser. No. 63/111,338, filed on Nov. 9, 2020, titled WCD SYSTEM WITH WIRELESS BATTERY CHARGING, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be mobile and personal. Mobile and personal healthcare devices may include Wearable Medical Devices (WMDs). Some WMDs may include medical devices that facilitate monitoring and treatment of various health related activities of a person. For example, a WMD may include a medical device that may be used to monitor a person's heart activity, including treatment of the heart. The heart activity monitored by the WMD may be in the form of electrical signals (i.e., electrocardiogram or ECG). Treatment of the heart may be in the form of a defibrillating shock, which may be administered responsive to the monitoring detecting a condition to trigger the treatment.

A WMD may be in a mobile form factor such as, but not limited to, a wearable support structure capable of being worn by a person, whose heart activity is to be monitored. Having the WMD in a mobile form factor may facilitate continuous monitoring of a person's ECG, which may facilitate detection of heart related issues, including treatment of the heart related issues.

An example of a WMD in a mobile form factor, which may be used to monitor and facilitate therapy of a person's heart activity, may be a wearable cardioverter defibrillator (WCD). Some examples of WCDs may include various components such as, but not limited to, electrodes. Some of the electrodes may be configured to monitor the person's heart activity (e.g., electrocardiogram or ECG electrodes). Some electrodes may be configured to facilitate providing an electrical shock to the person (e.g., therapy electrodes). Various electrical activities of the WCD may be performed by various electronic components (e.g., a processor for monitoring and/or analysis of the person's heart activity, indication signals, a display, an energy storage device, transmitting electrical signals to the electrodes for defibrillations, a user interface, etc.). Many of these electronic components may be powered by an energy storage device such as, but not limited to, a battery.

Commonly, the battery may be removable to facilitate being replaced with a spare battery, while the other battery is being recharged. In order to accommodate a removable battery, the WCD may include one or more openings to receive and house the battery. These openings may include various mechanical parts, including various moving parts (e.g., battery door, latch, hinge, etc.). In order to facilitate robustness and reliability of these mechanical parts, the mechanical parts may be bulky, which in turn may add bulkiness to the WCD (e.g., WCD monitor). Even with the with robustness of the mechanical parts, eventually, the mechanical parts may be or become susceptible to damage through operation of the moving parts, repeated insertion/removal cycles, and intrusion into the opening(s) of the monitor unit of moisture (e.g., sweat, gel, water, water vapor in humid air, etc.) and/or other contaminants (e.g., dirt, dust).

Additionally, a WCD may be used by an elderly person or by a person who may have healthcare issues that may make it difficult for the person to remove and install batteries quickly and correctly. Further, the removable batteries may be inadvertently removed or disconnected from the monitor unit, which may interrupt the monitoring process and may cause the WCD to issue one or more alarms. These avoidable alarms may be irritating and stressful to the person.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative wearable healthcare systems, which may be worn by a person. Example wearable healthcare systems may include a wearable cardioverter defibrillator (WCD). The example WCD may include a support structure, one or more monitor electrodes included in the support structure, one or more therapy electrodes included in the support structure, and a wearable cardioverter defibrillator (WCD) monitor communicatively coupled to the one or more monitor electrodes and to the one or more therapy electrodes. Example WCD monitor may include an energy storage device, where the energy storage device may be configured to be wirelessly rechargeable.

Additionally, described herein are various WCD monitor. Example WCD monitor may include a processor and a wireless charging module communicatively coupled to the processor. The WCD monitor may include an energy storage device communicatively coupled to the wireless charging module, where the energy storage device may be configured to be irremovable.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to apparatus and systems related to a wearable medical device (WMD) having wirelessly rechargeable energy storage device.

In the present disclosure, a wearable medical device (WMD) may include a medical device that may be configured to facilitate monitoring and treatment of potential issues with a person's heart (i.e., the person may have a health condition, where the electrical control system of the heart may malfunction causing the heart to beat irregularly or not at all). Commonly, these types of medical devices may include a defibrillator device (e.g., a wearable cardioverter defibrillator or WCD). In the present disclosure, the WCD may be include a wirelessly rechargeable energy storage device. Accordingly, the disclosure will be described referencing medical devices having a wirelessly rechargeable energy storage device, in accordance with various embodiments.

Briefly, the above mentioned issue with the rate of the heartbeat may be generally referred to as arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the medical device configured to be utilized to help treat VF by defibrillating the heart, the medical device may be capable of monitoring the electrical signals of the person's heart, and if necessary, administer therapy to the heart in the form of an electric shock. The medical device may monitor the electrical signals and provide the electric shock to the heart externally (i.e., through the surface of a body) via components commonly known as electrodes. The medical device may be in the form of a cardioverter defibrillator. The medical device may be included in a support structure configured to be worn by the person. In this example, the medical device may help facilitate monitoring the electrical activities of the person's heart and providing the electric shock to the heart in the VF condition. As a result, the medical device may help prevent Sudden Cardiac Death (SCD).

In various embodiments, the medical device may include a wirelessly rechargeable energy storage device (hereon battery) to provide the power for the various electronic components of the medical device. For example, the medical device may include a battery, a processor, a display, a storage medium, various number of electrodes to facilitate monitoring (e.g., monitor electrodes) of the electrical signals of the heart, a couple of electrodes to administer an electric shock as treatment (e.g., therapy electrodes), and numerous circuitry to facilitate proper functionality of various electronic components. As part of the monitoring (e.g., arrhythmia detection), the medical device may be configured to receive electrocardiogram (ECG) signals from the number of monitor electrodes (e.g., 5 ECG electrodes) located on the skin of a person. If the received ECG signals indicate a potential arrhythmia event, the medical device may be configured to provide a defibrillating shock to the person's heart via the therapy electrodes. In accordance with various embodiments, when the battery needs to be recharged, the battery may be wirelessly recharged.

Before turning to the figures, a non-limiting example configurations and utilization of the various embodiments of the present disclosure may be described. In the non-limiting example, a WCD may be worn by a person. The WCD may include a WCD monitor, which may include various electronic components to facilitate the functionality of the WCD as previously described. The various electronic components of the WCD monitor may be powered by a battery. The battery may be irremovably included in the WCD because the battery may be wirelessly rechargeable, in accordance with various embodiments.

Continuing with the example of the WCD worn by a person, the WCD monitor may include a wireless charging component such as, but not limited to, an inductive charging component. The inductive charging component may be configured to conform to a standard such as, but not limited to, Qi wireless power transfer standard. The inductive charging component included the WCD may be communicatively coupled to the battery to facilitate charging of the battery. In this example, the person wearing the WCD may place the WCD within proximity to an inductive charging device such as, but not limited to, a Qi compatible charging pad. For example, a pad or a blanket may be Qi compatible for charging. The person may place the WCD on the pad to facilitate charging, or the person may cover themselves in the blanket to facilitate charging.

In some examples, the WCD may include sensors and/or accessories that may be wirelessly communicatively coupled to the WCD monitor (hereon wireless sensors). In this example, a wireless charging system may be configured to wirelessly charge these wireless sensors. An example of a wireless sensor that may be a smartphone type device. The smartphone type device may be included as part of the WCD, and the smartphone type device may be wirelessly charged as well.

Continuing with the example of the WCD having wireless sensors coupled to the WCD monitor, in some examples, the wireless sensors may be incorporated into a garment that may be worn by the person. For example, the garment may be made of metamaterial based conductive textiles, which may be configured to form a wireless body sensor network such as those described in http://news.nus.edu.sg/research/nus-innovation-boosts-wireless-connectivity-1000-times and Tian, X., Lee, P. M., Tan, Y. J. et al., *Wireless body sensor networks based on metamaterial textiles*, Nature Electronics 2, 243-251 (2019), https://doi.org/10.1038/s41928-019-0257-7 (abstract at https://www.nature.com/articles/s41928-019-0257-7).

As described in these publications, in addition to enabling improved privacy and improved power savings in the wireless transmission of data to/from the wireless sensors, power may be transmitted from the WCD monitor to the wireless sensors. In some examples, the metamaterial based conductive textiles may be configurable to operate with transmission type wireless charging. For example, transmission type wireless charging may be of the type known as Cota® charging from Ossia, Inc. of Bellevue, Washington Having a garment made of metamaterial based conductive textiles configured to facilitate transmission type wireless charging may provide a larger area to capture the transmitted energy for charging the battery included in the WCD monitor.

In some examples, the WCD monitor may be separately charged, while the WCD may be continually worn by the person. For example, the WCD monitor may be removed from the support structure, while being communicatively coupled to the WCD, and the WCD may be placed on a nightstand. The nightstand may have a wireless charging device such as, but not limited to, a Qi charging pad, a Cota® charging receiver/transmitter, and so on. The person may place the WCD monitor on the charging pad while sleeping thereby facilitating charging of the battery included in the WCD monitor.

In some examples, two or more WCD monitors may be utilized to facilitate a changeout of the WCD monitors. For example, two or more WCD monitors may include a quick connect/release type connector coupling with the WCD. The person may disconnect one WCD monitor and place on a wireless charging device (e.g., Qi pad), while a second WCD monitor may be coupled to the WCD. In some examples, the quick connect/release type connector coupling may include magnetic connectors used with inductive wireless chargers such as, but not limited to, magnetic connectors disclosed at https://magnetmount.co/. In other examples, other types of connector mechanisms that are easy to disconnect/disengage can be used such as, but not limited to, light adhesive layers, retaining clips, snaps, hook/loop, and so forth. Such examples may reduce the size of the wireless charging device, while facilitating disconnection if the patient forgets about the charger connection when moving around or getting out of bed. Additionally, the second WCD monitor may be utilized to help facilitate diagnosis of potential issues with the first WCD monitor. For example, if replacing the first monitor unit with the second monitor unit results in the WCD working properly, the potential issue may be with the first WCD monitor. Further, the second WCD monitor may be utilized as a back-up in case of issues/failure of the first WCD monitor that may not be able to be addressed.

Prior to removing the WCD monitor, the monitor may be properly shut down. Accordingly, if the battery level reaches a low level and/or is about to be depleted, the WCD monitor may utilize a backup power source within WCD monitor to facilitate a proper shutdown. One methodology for this type of proper shutdown may be to utilize a capacitor included in the WCD monitor (e.g., the capacitor utilized to provide defibrillation shocks). The capacitor may be utilized to provide the energy to keep the processor, that may be included in the WCD monitor, long enough so that WCD monitor may not cause the WCD monitor perform a full boot-up process when the second WCD monitor is coupled to the WCD. Commonly, a full boot-up may occur when there is a power loss. Further, the capacitor may be charged with sufficient power to perform housekeeping tasks related to powering off such as, but not limited to, closing log and data acquisition files and putting high voltage therapy circuits into a safe state in case the patient has trouble coupling the second WCD monitor.

The wireless charger device may be incorporated in a wide variety of formfactors such as, but not limited to a bedsheet, blanket, comforter, mattress pad, etc. ("Blanket"). For inductive type charger examples, several coil units may be distributed throughout the Blanket having logic to determine which of the coil units may be closest to the corresponding coil unit on the device. Such examples may be advantageously used with WCDs that are adhesively attached to the patient such as those disclosed in U.S. Published Patent Application 20170056682 or in WCDs in which one or more batteries for the WCD may be attached to or may be integrated into a shirt, harness, belt, vest, garment etc. ("Support Structure") worn by a person.

In some examples, the WCD may include a base station that may be configurable to provide a communication hub functionality and be communicatively coupled to a server or communication network to transfer information (e.g., person's healthcare data, WCD status data, WCD configuration data, software updates, battery level, etc.) to and from the server or communication network. Additionally, the wireless charging system can be combined or integrated into the base station. In some examples, the base station may include a wired charging port for use with WCD monitors that may include a charging port (e.g., a dedicated port, USB port, etc.). The communicatively coupling of these base stations may include physical couplings and/or wireless couplings. For example, the WCD may include wireless communication methodologies such as, but not limited to, Wi-Fi, IEEE 802 based, Bluetooth® type, Near Field Communication (NFC), radio-frequency identification (RFID), ad-hoc wireless network solutions (e.g., AirDrop), internet of things (IoT) related communication solutions, mesh local area network (LAN) type (e.g., ZigBee, Bluetooth Low Energy, Z-Wave, 6LoWPAN, Thread, etc.), and any combination thereof. Accordingly, the WCD monitor may be configured to communicate with various remote devices such as, but not limited to, a smart phone type device, a tablet type device, a server type device, cloud networks, and so forth.

Even though the above non-limiting example may have been described with respect to a battery being included in a WCD monitor, in some examples, the battery may be located separately from the WCD monitor. For example, a battery may be included in various locations of a WMD having a garment type support structure such as, but not limited to, a back portion, a front portion, a side portion, etc. Additionally, a wireless charging module included in the WMD may be located separately from the battery. For example, the battery may be located in the back area, while the wireless charging module (inductive or transmission type) may be located in the front of the WMD. The battery and the wireless charging module may be communicatively coupled to facilitate the charging of the battery by the wireless charging module. Accordingly, the claimed subject matter is not limited in these respects.

Referring to the above non-limiting example configurations and utilization, in one example, the person may wear the WMD having the battery included in the back portion of the garment. The WMD may have the wireless charging module (e.g., inductive or transmission type) included in the front portion. In this example, the person may lie on their back and place a blanket over their front portion. The blanket may include a complimentary wireless charging module such as, but not limited to, a Qi wireless charging pad. This may facilitate wireless charging of the battery, which is located in the back of the WMD via the wireless charging module, which is located in the front of the WMD. The battery and the wireless charging module may be communicatively coupled.

In another example, the person may wear the WMD having the battery included in the back portion of the garment, and again, the wireless charging module may be included in the front portion of the WMD. The wireless charging module may be of the transmission type. An area or a room may be configured to have Cota® charging capabilities. In this example, the battery may be wirelessly charged by receiving the charging transmission on the front of the WMD, which may include as the person moves around the area or room having the Cota® charging capabilities.

The battery may be a variety of rechargeable batteries such as but not limited to nickel-cadmium (Ni—Cd), nickel metal hydride (Ni-MH), lithium-ion (Li-Ion), lithium polymer (Li—Po), etc. The form factors may include a wide variety to facilitate being included in the WMD (e.g., the wearable garment of the WMD). For example, the battery, which may be included in the WMD, may be a flexible type battery. For example, the battery may be a flexible lithium polymer battery available from Jenax, Inc. of Saengnimmyeon, Gimhae, Gyeongsangam-do, South Korea. Accordingly, the claimed subject matter is not limited in these respects.

The above non-limiting example configurations and utilization of the various embodiments of the present disclosure may facilitate wirelessly recharging an energy storage device (e.g., battery) included in a WCD monitor, where the battery may be irremovable from the WCD monitor. As a result, the WCD monitor may have reduced number of moving parts, which may improve reliability and durability. For example, the mechanical structures, including the battery connector and the battery contacts on the WCD monitor, may be reduced in size and weight to improve wearability of the WCD. Additionally, the WCD monitor may be sealed to reduce intrusion of moisture and other contaminants (e.g., reduce the potential for ingress of dust, moisture, etc.), which may facilitate wearing of the WCD while bathing, swimming, etc. Further, the WCD of the disclosure may be continually worn (i.e., the person's health may be continually monitored), while the battery is charged (e.g., Qi pad and wireless transmission charging).

It should be appreciated that after review of this disclosure that the above example components are just a few examples, and accordingly, electronic components of a medical device monitor may include a wide variety of electronic components to facilitate operation of the medical device. Some of details of the medical device will be described below with respect to FIG. 4.

Figure 1:
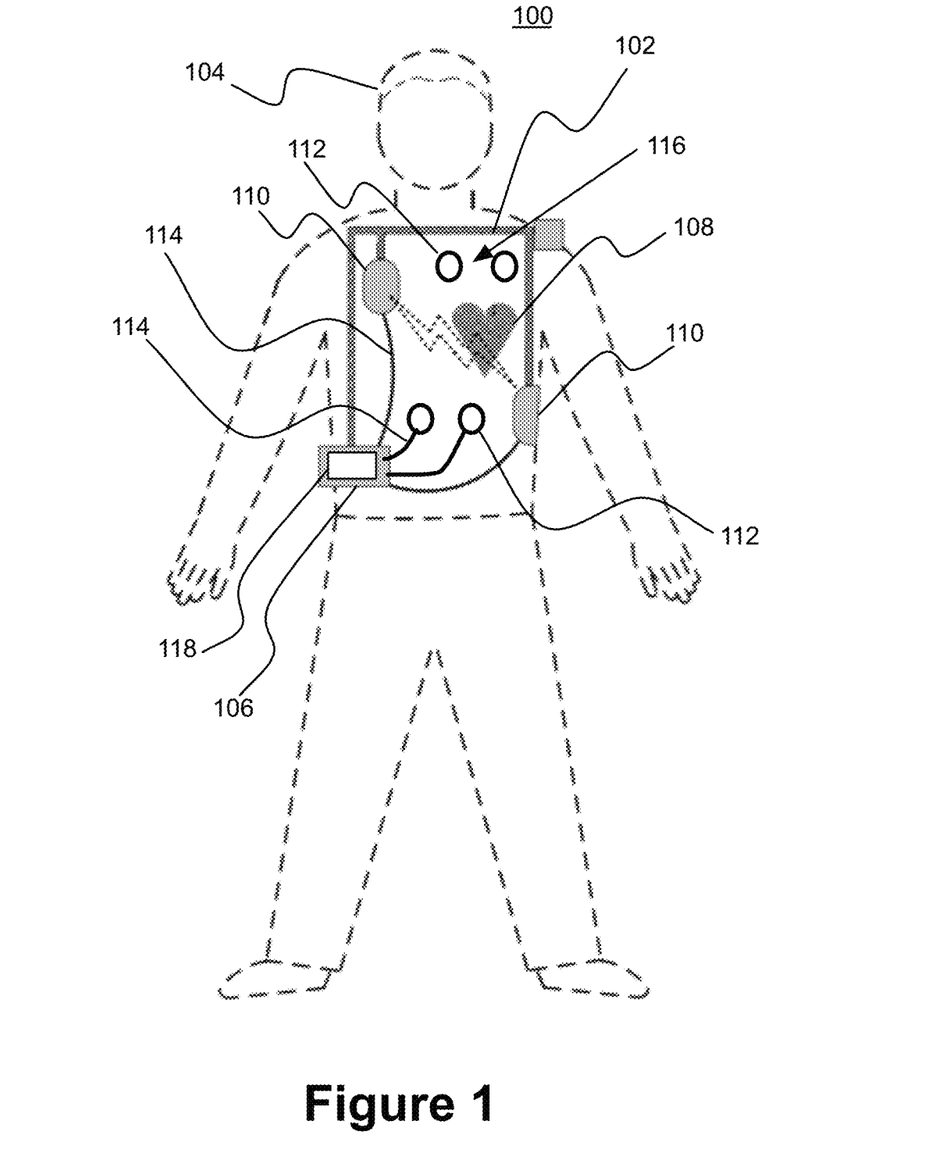
FIG. 1 illustrates a wearable medical device (WMD), in accordance with various embodiments.

Turning now to FIG. 1, FIG. 1 illustrates a wearable medical device (WMD), in accordance with various embodiments. In FIG. 1, a WMD may be configured to facilitate monitoring and treatment of a person's heart such as, but not limited to, a wearable cardioverter defibrillator (WCD) 100. The WCD 100 may be included in a support structure 102, which may be configured to be worn by a person 104. The WCD 100 may include various electronic components to facilitate the functionality of the WCD 100 as a heart monitoring and defibrillator device. The various electronic components may be illustrated as a WCD module (hereon a WCD monitor 106). The WCD 100 may include two therapy electrodes configured to defibrillate a person's heart 108, defibrillator electrodes 110, and a number of monitoring electrodes 112 configured to detect and measure the person's electrical heart activity (e.g., electrocardiogram or ECG). As shown, the monitoring electrodes 112 and the defibrillator electrodes 110 may be located proximate to the person's heart 108 and chest area 116. The monitoring electrodes 112 and the defibrillator electrodes 110 may be communicatively coupled to the WCD monitor 106 via a number of electrical leads 114. Additionally, shown in FIG. 1, the WCD monitor 106 may include an energy storage device (hereon a battery 118).

In FIG. 1, the support structure 102 may be in the form of a garment configured to be worn by the person 104. In some examples, support structure 102 may be made of metamaterial textiles.

In some examples, the monitoring electrodes 112 and the defibrillator electrodes 110, shown in FIG. 1, may be configured to be wirelessly coupled with the WCD monitor 106.

In one example, the WCD monitor 106 may be configured to be included in the support structure 102. In another example, the WCD monitor 106 may be configured to decouplable from the WCD 100 facilitating swappable two or more WCD monitors. The Swappable WCD monitors may include quick release/connect features.

As described herein, the battery 118 included in the WCD monitor 106 may be configured to be wirelessly rechargeable, in accordance with various embodiments. Examples of wireless charging methodologies may include wireless charging methodologies utilizing inductive wireless charging. Inductive wireless charging may include Qi wireless charging standard developed by the Wireless Power Consortium, Logitech Powerplay wireless charging available from Logitech International S.A. of Lausanne, Switzerland, MagSafe wireless charging available from Apple Inc. of Cupertino, California, etc. Some additional examples of wireless charging methodology may include direct transmission wireless charging such as, but not limited to, Cota® wireless transmission charging available from Ossia Inc. of Redmond, Washington. Accordingly, the claimed subject matter is not limited in this respect. Additionally, because of the wirelessly chargeable configuration of the battery 118, the battery 118 may be configured to be irremovable.

Figure 2:
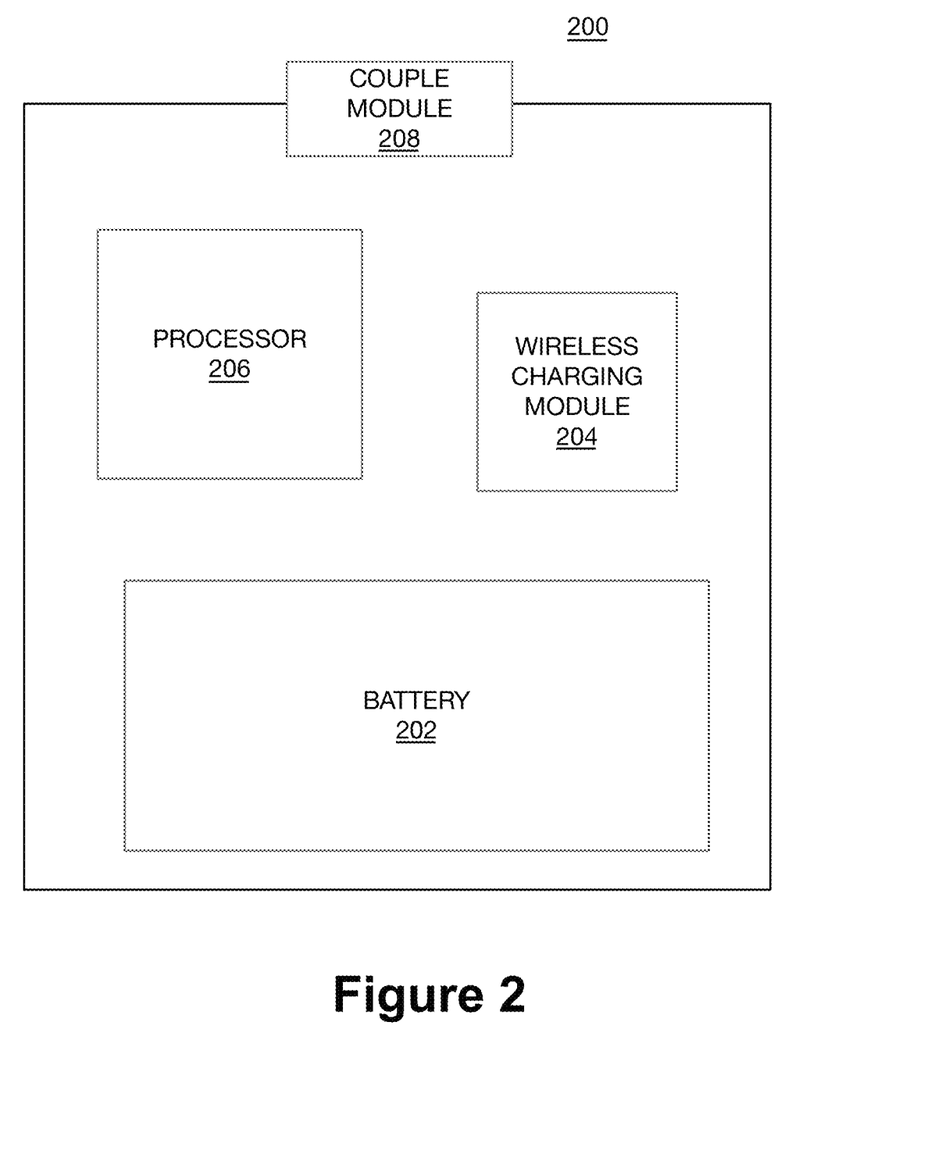
FIG. 2 is a block diagram of a WCD monitor having an energy storage device, in accordance with various embodiments.

FIG. 2 is a block diagram of a WCD monitor having an energy storage device, in accordance with various embodiments. In FIG. 2, a WCD monitor 200 may be similar to the WCD monitor 106 shown in FIG. 1. Shown in FIG. 2, the WCD monitor 200 may include an energy storage device (battery 202), a wireless charging module 204, a processor 206, and a couple module. Since the WCD monitor 200 may be a simplified block diagram, various components have been omitted clearly describe the claimed subject matter and not obscure it.

In FIG. 2, the processor 206 may be communicatively coupled to the wireless charging module 204. Under the control of the processor 206, the wireless charging module 204 may be configured to charge the battery 202. The wireless charging module 204 may be a wide variety of wireless charging modules such as, but not limited to, inductive wireless charging module, transmission wireless charging module, and so forth.

The couple module 208, shown in FIG. 2, may be illustrative of a wide variety of couple module such as, but not limited to, a quick release/connect couple module, a number of separate couple module, wireless communication couple module, a physical connection couple module, and so forth.

Figure 3:
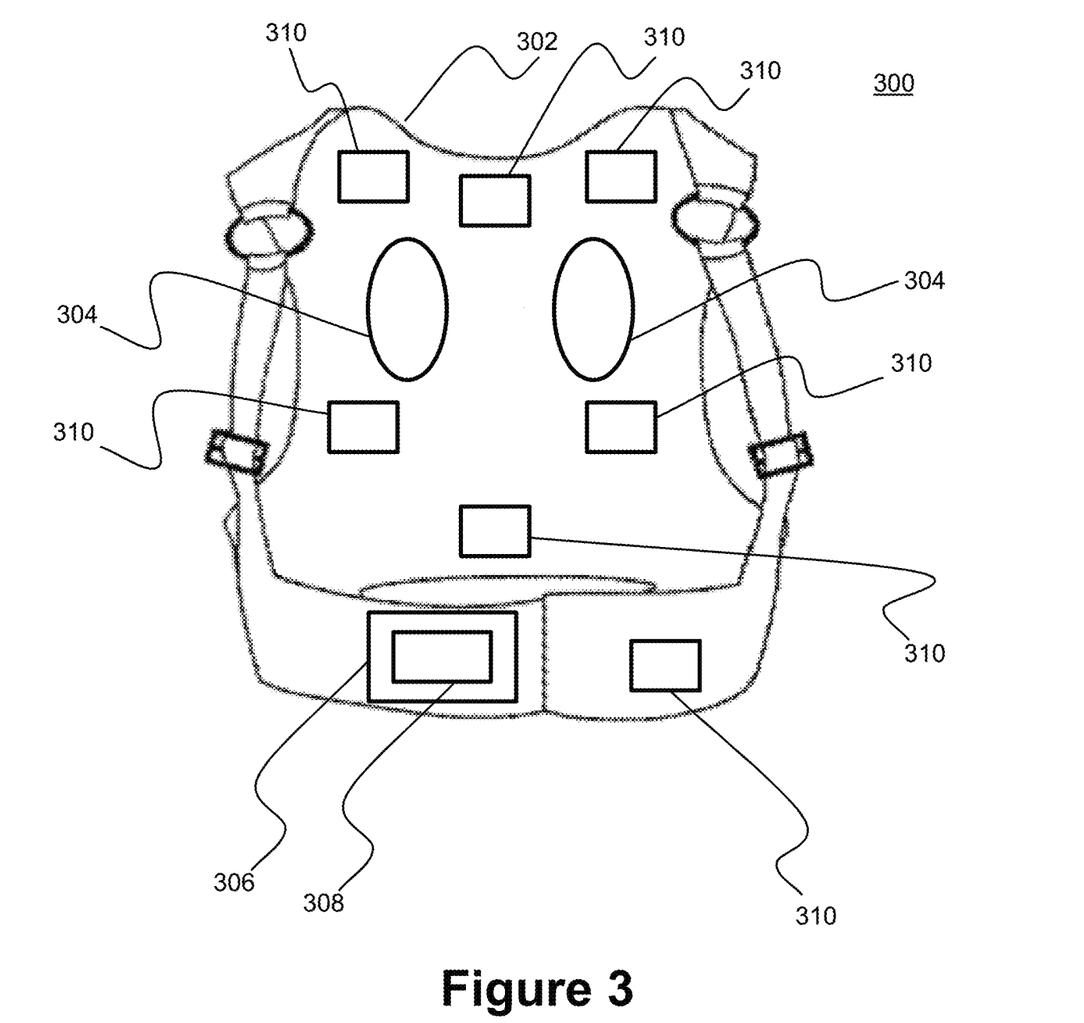
FIG. 3 illustrates a WMD having an integrated number of wireless sensors, in accordance with some embodiments.

FIG. 3 illustrates a WMD having an integrated number of wireless sensors, in accordance with some embodiments. In FIG. 3, a WMD may be configured to be a WCD 300 such as the WCD 100 to be utilized by the person 104 (shown in FIG. 1). In FIG. 3, a support structure 302 of the WCD 300 may be in the form of a clothing having the shape of a vest. The WCD 300 may include at least one or more WCD components such as, but not limited to, two electrodes 304 (e.g., defibrillator electrodes as previously described), a WCD monitor 306, an energy storage device (battery 308) included in the WCD monitor 306, and one or more sensors and/or accessories (electronic components 310). The one or more electronic components 310 may be one or more sensors and/or accessories as previously described. In accordance with the present disclosure, the battery 308 may be configured to be wirelessly rechargeable.

Shown in FIG. 2, the one to more electronic components 310 may be distributed within the WCD 300 as shown (i.e., dispersed throughout the vest). Each of the one or more electronic components 310 may be communicatively coupled to the WCD monitor 306. For example, support structure 302 may comprise of metamaterial textiles, which may facilitate communicatively coupling the one or more electronic components 310 with various other components of the WCD 300 (e.g., with the two electrodes 304 and the WCD 306) to facilitate the proper function of the WCD 300 (i.e., monitor and defibrillate a person's heart 108 (shown in FIG. 1). In one example, the one or more electronic components 310 may be communicatively coupled via physical electrical connections. In another example, the electronic components 310 may be communicatively coupled via wireless communicative coupling.

Referring back to the non-limiting example scenario above, the one or more electronic components 310, the two electrodes 304, and the WCD monitor 306 may be communicatively coupled via wires sewn into the fabric of the clothing. In some embodiments, the two electrodes 304 may be electrodes that both sense ECG and provide defibrillation and/or pacing therapy. In other embodiments, the two electrodes 304 are defibrillator electrodes and additional ECG electrodes are used to sense the patient's ECG signals. In another example, the one or more electronic components 310, the two electrodes 304, and the WCD monitor 306 may be communicatively coupled wirelessly utilizing wireless protocols such as but not limited to, Bluetooth® type, IEEE 802 based, mesh local area network (LAN) type (e.g., ZigBee, Bluetooth Low Energy, Z-Wave, 6LoWPAN, Thread, etc.), and any combination thereof. Alternatively, the one or more electronic components 310 may be communicatively coupled wirelessly with the WCD 306, while the two electrodes 304 may be communicatively coupled via wires with the WCD 306. For example, in the case of the two electrodes 304 being used for both therapy and ECG sensing, the wires can be used to deliver charge for therapy, while the wireless link can be used to communicate ECG signals, thereby protecting the ECG sensors from potential damage when therapy is delivered to the person 104.

In yet another example, the material of the support structure 302 may be made of smart textiles having integrated conductive textiles to facilitate communicatively coupling the one or more electronic components 310 such as, but not limited to, wireless body sensor networks based on metamaterial textiles. The support structure 302 may include one or more electronic components 310 with the metamaterial textiles forming a number of metamaterial structures integrated into the clothing such as, for example, described above example references. One of the one or more electronic components 310 may be wirelessly coupled to one of the one or more electronic modules 310 via the number of metamaterial structures. For example, the one or more electronic modules may include one or more ECG type sensors with the ECG type sensors being textile based electrodes integrated in the support structure 302.

Figure 4:
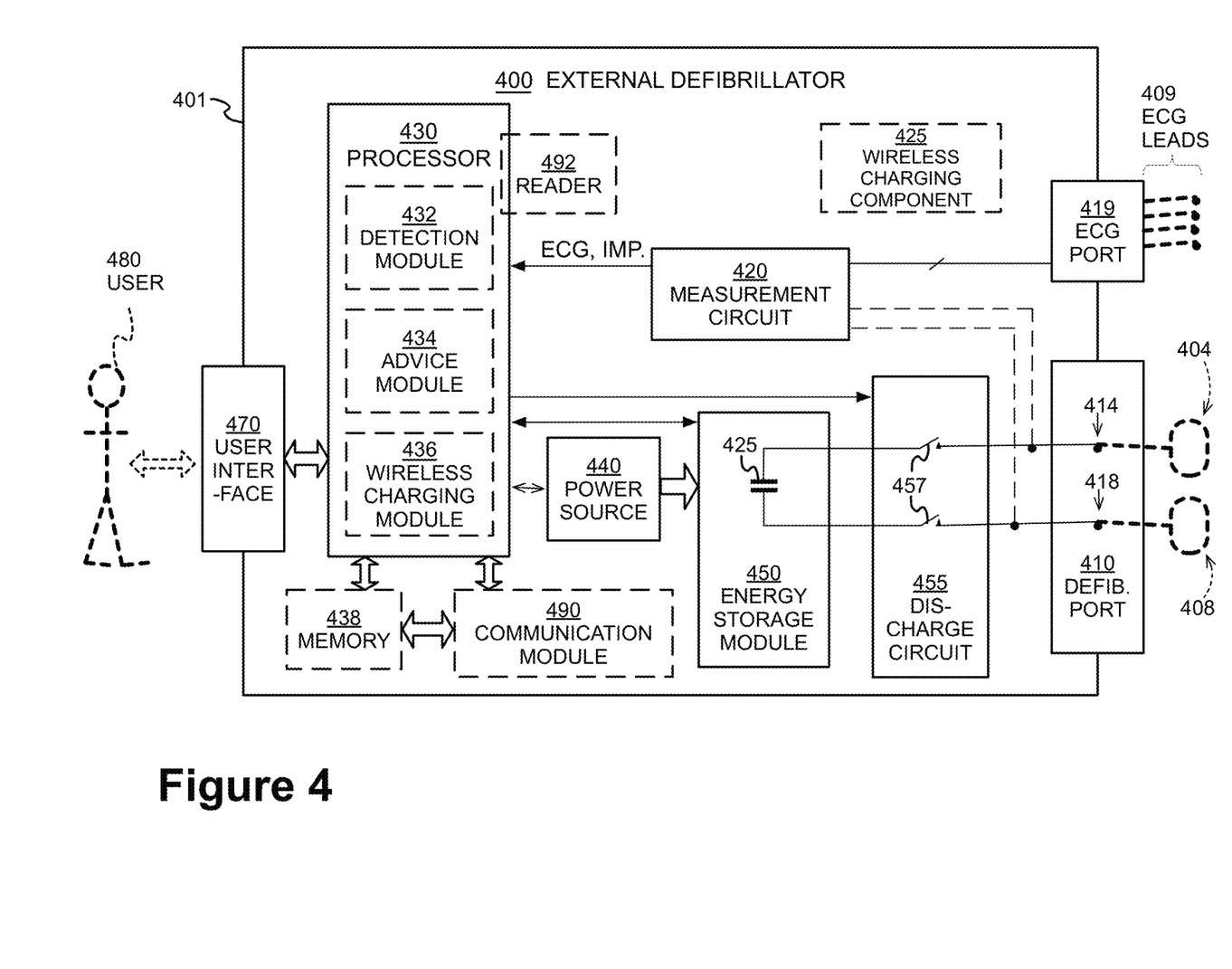
FIG. 4 is a block diagram illustrating components of wearable medical device having a wirelessly rechargeable energy storage device, in accordance with various embodiments.

FIG. 4 is a block diagram illustrating components of wearable medical device having a wirelessly rechargeable energy storage device, in accordance with various embodiments. These components may be, for example, components of medical device such as, but not limited to, a WCD monitor 106, 200, and 306 (shown in FIGS. 1, 2, and 3).

The defibrillator device 400 may be some of the above examples of a one or more modules for the medical device (e.g., the WCD monitor 200 shown in FIG. 2) intended for use by a user 480 (e.g., a wearer, person, patient, etc.). The defibrillator device 400 may typically include a defibrillation port 410, such as a socket in housing 401. The defibrillation port 410 may include nodes 414 and 418. One or more electrodes 404 and 408, which may be removably plugged into the defibrillation port 410, so as to make electrical contact with nodes 414 and 418, respectively. It may also be possible that the electrodes 404 and 408 may be connected continuously to the defibrillation port 410, etc. Either way, the defibrillation port 410 may be used for guiding via the electrodes 404 and 408 to the user 480 an electrical charge that may have been stored in the defibrillator device 400, as described herein. Additionally, the defibrillation port 410 may be configured to be of quick release/connect type to facilitate coupling and decoupling the defibrillator device 400 (e.g., WCD monitor) from the electrodes for recharging, as described above.

The defibrillator device 400 may also have an ECG port 419 in the housing 401, for receiving ECG cables 409. The ECG cables 409 may facilitate sensing of an ECG signal (e.g., a 12-lead signal or from a different number of lead signals). Moreover, a defibrillator-monitor could have additional ports (not shown) making the defibrillator device 400 more reconfigurable, and the other component 425 may be configured to filter the ECG signal (e.g., application of at least one filter to the signal to help facilitate removal of artifacts such as, but not limited to, chest compression due to chest compressions being delivered to the person). Additionally, the ECG port 519 may be configured to be wirelessly communicatively coupled with one or more electronic components such as, but not limited to, ECG electrodes 112 (shown in FIG. 1). Further, the ECG port 419 may be configured to be of quick release/connect type to facilitate coupling and decoupling the defibrillator device 400 (e.g., WCD monitor) from the electrodes for recharging, as described above.

The defibrillator device 400 also may include a measurement circuit 420. The measurement circuit 420 may receive physiological signals from the ECG port 419, and also from other ports, if provided. The circuit 420 may render detected physiological signals and their corresponding information. The information may be in the form of data, or other signals, etc.

The defibrillator device 400 may also include a processor 430. The processor 430 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 430 may include a number of modules. One example module may be a detection module 432, which may detect outputs from the measurement circuit 420. The detection module 432 may include a VF detector. Accordingly, the person's detected ECG may be utilized to help determine whether the person is experiencing ventricular fibrillation (VF).

In another example module may be an advice module 434, which may provide advice based, at least in part, on outputs of detection module 432. The advice module 434 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator device 400 may further issue prompts for administrating CPR, and so forth.

The processor 430 may include additional modules, such as a wireless charging module 436 for managing various wireless charging functionalities as described with respect to FIG. 2. Accordingly, the wireless charging component 425 may be operated in part by the processor 430. The wireless charging component 425 may include inductive wireless charging components, transmission wireless charging components, and so forth, as described above.

In an example, the defibrillator device 400 may include a memory 438, which may work together with the processor 430. The memory 438 may be implemented in a wide variety of manners. For example, the memory 438 may be implemented such as, but not limited to, nonvolatile memories (NVM), read-only memories (ROM), random access memories (RAM), and so forth or any combination thereof. The memory 438 may can include programs for the processor 430, and so on. The programs may include operational programs execution by the processor 430 and may also include protocols and methodologies that decisions may be made by advice module 434. Additionally, the memory 438 may store various prompts for the user 480, etc. Moreover, the memory 438 may store a wide variety of information (i.e., data) such as, but not limited to information regarding the person.

The defibrillator 400 may also include a power source 440. In order to facilitate portability of defibrillator device 400, the power source 440 may include a battery type device. A battery type device may be implemented as a battery pack, which may be rechargeable. However, at times, a combination of rechargeable and non-rechargeable battery packs may be utilized. Additionally, the power source may be configured to be modified to accommodate the power level demands (e.g., monitoring mode without therapy or vice versa). Examples of power source 440 may include AC power override, where AC power may be available, and so on. In some examples, the processor 430 may control the power source 440. As described, the power source 440 may be configured to be irremovable and be configured to be wirelessly rechargeable, in accordance with various embodiments.

Additionally, the defibrillator device 400 may include a configurable energy storage module 450. The configurable energy storage module 450 may be configured to store some electrical energy (e.g., when preparing for sudden discharge to administer a shock). The configurable energy storage module 450 may be charged from the power source 440 to an appropriate level of energy, as may be controlled by the processor 430. In some implementations, the configurable energy storage module 450 may include one or more capacitors 452, and the like.

The defibrillator device 400 may include a discharge circuit 455. The discharge circuit 455 may be controlled to facilitate discharging of the energy stored in energy storage module 450 to the nodes 414 and 418, and also to electrodes 404 and 408. The discharge circuit 455 may include one or more switches 457. The one or more switches 457 may be configured in a number of manners such as, but not limited to, an H-bridge, and so forth.

The defibrillator device 400 may further include a user interface 470 for the user 480. The user interface 470 may be implemented in a variety of manners. For example, the user interface 470 may include a display screen capable of displaying what is detected and measured, provide visual feedback to the user 480 for their resuscitation attempts, and so forth. The user interface 470 may also include an audio output such as, but not limited to, a speaker to issue audio prompts, etc. The user interface 470 may additionally include various control devices such as, but not limited to, pushbuttons, touch display, and so forth. Additionally, the discharge circuit 455 may be controlled by the processor 430 or directly by the user 480 via the user interface 470, and so forth.

Additionally, the defibrillator device 400 may include other components. For example, a communication module 490 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

The above described components may be configured and reconfigured, in accordance with various embodiments. For example, monitoring mode or monitoring and therapy mode.

It should be appreciated after review of this disclosure that it is contemplated within the scope and spirit of the present disclosure that the claimed subject matter may include a wide variety of healthcare devices. Accordingly, the claimed subject matter is not limited in these respects.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. A wearable medical device (WMD) system including a WMD, the WMD system comprising:
    a support structure configured to be worn by a patient;
    one or more monitor electrodes that include a wireless sensor, the one or more monitor electrodes coupled to the support structure, the one or more monitor electrodes configured to receive electrical signals from a heart of the patient;
    one or more therapy electrodes, the one or more therapy electrodes configured to provide defibrillation and/or pacing therapy from the WMD to the heart of the patient;
    a monitor that is wirelessly coupled to the wireless sensor and electrically coupled to the one or more therapy electrodes via a wire;
    an energy storage device to provide power to the monitor; and
    a blanket configured to wirelessly recharge the wireless sensor and the energy storage device when the blanket is used by the patient to cover at least a portion of the WMD system.

2. The WMD system of claim 1, wherein the one or more monitor electrodes comprise an electrocardiogram (ECG) electrode.

3. The WMD system of claim 1, wherein the monitor does not have a charging port.

4. The WMD system of claim 1, wherein the monitor comprises the monitor being included in the support structure.

5. The WMD system of claim 1, wherein the energy storage device comprises a capacitor configured to provide power to be used to perform a task related to powering off the monitor.

6. The WMD system of claim 1, wherein the energy storage device comprises an irremovable battery.

7. The WMD system of claim 1, wherein the blanket is configured to wirelessly recharge the energy storage device using inductive charging.

8. The WMD system of claim 7, wherein the blanket comprises a plurality of coil units and the monitor comprises a coil unit used in inductive charging of the energy storage device.

9. The WMD system of claim 8, wherein the blanket further comprises logic to determine which of the plurality of coil units of the blanket is closest to the coil unit of the monitor.

10. The WMD system of claim 1, wherein the blanket comprises a bedsheet.

11. The WMD system of claim 1, wherein the blanket comprises a comforter.

12. The WMD system of claim 1, wherein the blanket comprises a mattress pad.

13. A wearable medical device (WMD) system including a WMD, the WMD system comprising:
    a support structure configured to be worn by a patient;
    one or more monitor electrodes that include a wireless sensor, the one or more monitor electrodes coupled to the support structure and configured to receive electrical signals from a heart of the patient;
    one or more therapy electrodes, the one or more therapy electrodes configured to provide an electric shock or pulse to the heart of the patient;
    a monitor communicatively wirelessly coupled to the wireless sensor and electrically coupled to the one or more therapy electrodes via a wire, the monitor comprising:
        an energy storage device,
        a wireless charging module,
        a processor, the processor communicatively coupled to the wireless charging module, and
        a couple module; and
    a blanket, wherein when the blanket is worn by the patient and the blanket covers at least a portion of the WMD system, the blanket is configured to:
    wirelessly recharge the energy storage device via the wireless charging module, and
    wirelessly recharge the wireless sensor.

14. The WMD system of claim 13, wherein the one or more monitor electrodes comprise an electrocardiogram (ECG) electrode.

15. The WMD system of claim 13, wherein the monitor does not have a charging port.

16. The WMD system of claim 13, wherein the monitor comprises a capacitor configured to provide power to the processor to perform a task related to powering off the monitor.

* * * * *